United States Patent
Fukushima et al.

(12) 
(10) Patent No.: US 6,252,056 B1
(45) Date of Patent: Jun. 26, 2001

(54) HUMAN LYSOPHATIDIC ACID RECEPTOR AND USE THEREOF

(75) Inventors: Daikichi Fukushima; Shinji Nakade; Hisanori Haga, all of Osaka (JP)

(73) Assignee: Ono Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/554,225

(22) PCT Filed: Nov. 10, 1998

(86) PCT No.: PCT/JP98/05047

§ 371 Date: May 11, 2000

§ 102(e) Date: May 11, 2000

(87) PCT Pub. No.: WO99/24569

PCT Pub. Date: May 20, 1999

(30) Foreign Application Priority Data

Nov. 11, 1997 (JP) .................................................... 9-307749

(51) Int. Cl.[7] .......................... C07H 21/02; C12P 21/06; C12P 19/34; C12N 1/20; C12M 1/02
(52) U.S. Cl. ........................ 536/23.1; 435/69.1; 435/91.1; 435/252.3; 435/320.1
(58) Field of Search .............................. 435/6, 91.1, 91.2, 435/69.1, 69.2, 183, 252.3, 320.1; 436/94; 536/23.1, 24.3, 24.33, 25.53; 530/300, 350, 333, 344, 355

(56) References Cited

PUBLICATIONS

Proc. Natl. Acad. Sci. USA, vol. 93 (1996), Z. Guo et al., "Molecular cloning of a high–affinity receptor for the growth factor–like lipid mediator lysophosphatidic acid from Xenopus oocytes", pp. 14367–14372.

R.W. Ould, S.B. Primrose, "Principles of Gene Manipulation", Feb. 25, 1991, K.K. Baifukan, p. 115.

Neuroscience Res., Suppl. 22 (Oct., 1998), Y. Kawasawa et al., "Cloning and Characterization of Mouse LPA Receptor (PSP24)", p. S89.

Faseb J., vol. 12 (Apr., 1998), Y. Kawasawa et al., "Cloning and Characterization of A Mouse Homologue of Xenopus PSP24 LPA Receptor", p. A1460.

Biochemical and Biophysical Research Communications, vol. 231, (1997), Article No. RC976150, S. An et al., "Molecular Cloning of the Human Edg2 Protein and Its Identification as a Functional Cellular Receptor for Lysophosphatidic Acid", pp. 619–622.

*Primary Examiner*—Ethan Whisemont
*Assistant Examiner*—Frank W. Lu
(74) *Attorney, Agent, or Firm*—Sughrue, Mion, Zinn, Macpeak & Seas, PLLC

(57) ABSTRACT

(1) A human lysophosphatidic acid (human LPA) receptor, (2) a method for screening an antagonist or agonist, comprising using a human LPA receptor protein, (3) an LPA inhibitor comprising the human LPA receptor, (4) a method for producing the human LPA receptor, (5) a monoclonal or polyclonal antibody against the human LPA receptor, (6) a cDNA encoding the human LPA receptor, (7) a replication or expression vector carrying the above cDNA, and (8) a host cell transformed with the above replication or expression vector.

11 Claims, 1 Drawing Sheet

EXPRESSION TEST OF RECEPTOR
EXCESS EXPRESSION CELL
(NORTHERN HYBRIDIZATION)

US 6,252,056 B1

HUMAN LYSOPHOSPHATIDIC ACID RECEPTOR AND USE THEREOF

TECHNICAL FIELD

The present invention relates to a lysophosphatidic acid (LPA) receptor and use thereof. More specifically, it relates to (1) a human LPA receptor, (2) a method for screening a human LPA-like substance, a human LPA antagonist and an antagonist or agonist for a phospholipid other than LPA capable of responding to the human LPA receptor, comprising using a human LPA receptor protein, (3) an LPA inhibitor or an inhibitor for a phospholipid other than human LPA, comprising the human LPA receptor, (4) a method for producing the human LPA receptor, (5) a monoclonal or polyclonal antibody against the human LPA receptor, (6) a cDNA encoding the human LPA receptor, (7) a replication or expression vector carrying the above cDNA, and (8) a host cell transformed with the above replication or expression vector.

BACKGROUND ART

It is known that LPA receptors bind LPA to transmit a signal into cells and induce various physiological phenomena, such as cell proliferation, dedifferentiation of vascular cells, inhibition of cell proliferation, and the like. Thus, if a human LPA receptor can be provided, not only its application as a medicament or diagnostic drug for vasospasm and the like can be expected using the human LPA receptor per se but also its broad contribution to the development of medicaments, such as screening and evaluation of medicaments, such as a new LPA receptor antagonist and the like, can be expected. Although it is known that plural kinds of LPA receptors are present, all kinds of human LPA receptors have not been isolated yet, and the actions and structures have not been specified.

Cells recognize various physiologically active substances, such as proliferation factors, hormones, neurotransmitters, and the like, via a receptor and response thereto in various manner. LPA receptors which are present on the cell membrane bind to LPA and transmit a signal into the cell via a G protein conjugated with the receptor. Gi, Gq and the like are known as G proteins which can be conjugated with LPA receptors, and it is considered that these receptors take part in responses, such as cell proliferation promoting action or, conversely, proliferation inhibiting action, and the like. Additionally, it has been found that an MAP-kinase system is connected with the downstream of the G protein and the LPA receptors transmit various signals.

Receptors using LPA as the ligand have been isolated from mouse and Xenopus. For example, Tigyi et al. have obtained an LPA receptor, called PSP24 LPA receptor, for the first time from Xenopus oocyte (*Proc. Natl. Acad. Sci. U.S.A.*, 93: 14367–14372 (1996)). Also, another kind of LPA receptor has been cloned from a mouse, which is called vzg-1 (*J. Cell. Biol.*, 135:1071–1083 (1996)).

As human origin LPA receptors, Edg-2 which is a homologue of vzg-1 has been reported (*Biochem. Bioph. Res. Commun.*, 231:619–622 (1997)); however, there are no reports on the PSP24 in human.

SUMMARY OF THE INVENTION

With the aim of cloning a human counterpart of the PSP24 LPA receptor which is expressed in Xenopus oocyte, the present inventors have conducted intensive studies and, as a result, succeeded in cloning a cDNA encoding a PSP24 human LPA receptor derived from a human brain tissue and in determining the complete amino acid sequence of the LPA receptor.

When the known nucleotide sequences registered in the nucleotide sequence database were searched by BLASTN, and the amino acid sequences of known polypeptides registered in the amino acid sequence database by BLASTP, there was no sequence which coincided with the nucleotide sequence encoding the PSP24 human LPA receptor. Also, it was expected based on a hydrophobic plotting analysis that the polypeptide of the LPA receptor has seven transmembrane domains. Accordingly, it was confirmed that this polypeptide is a novel membrane protein.

The present invention relates to:

(1) a protein comprising the amino acid sequence shown in SEQ ID NO:1, a homologue thereof, a fragment thereof, or a fragment of the homologue thereof;

(2) a human lysophosphatidic acid (human LPA) receptor comprising the amino acid sequence shown in SEQ ID NO:1 or a homologue thereof;

(3) a method for screening a human LPA-like substance, a human LPA antagonist, and an antagonist or agonist for a phospholipid other than LPA capable of responding to the human LPA receptor, comprising using the protein according to the above (1) or (2);

(4) a human LPA inhibitor or an inhibitor for a phospholipid other than human LPA, comprising the protein according to the above (1) or (2) as an active ingredient;

(5) a method for producing a human LPA receptor, comprising culturing a cell transformed with an expression vector carrying a DNA fragment encoding the protein according to the above (1) or (2), and recovering the protein from the cultured mixture;

(6) a monoclonal or polyclonal antibody against the protein according to the above (1) or (2) or a peptide comprising a partial sequence of the protein;

(7) a cDNA encoding the polypeptide according to the above (1) or (2);

(8) a fragment which selectively hybridizes to the cDNA according to the above (7) comprising the nucleotide sequence shown in SEQ ID NO:2, or a sequence thereof;

(9) a fragment which selectively hybridizes to the cDNA according to the above (7) comprising the nucleotide sequence shown in SEQ ID NO:3, or a sequence thereof;

(10) a replication or expression vector carrying the cDNA according to any one of the above (6) to (9); and

(11) a host cell transformed with the replication or expression vector according to the above (10).

DETAILED DESCRIPTION

Figure 1:
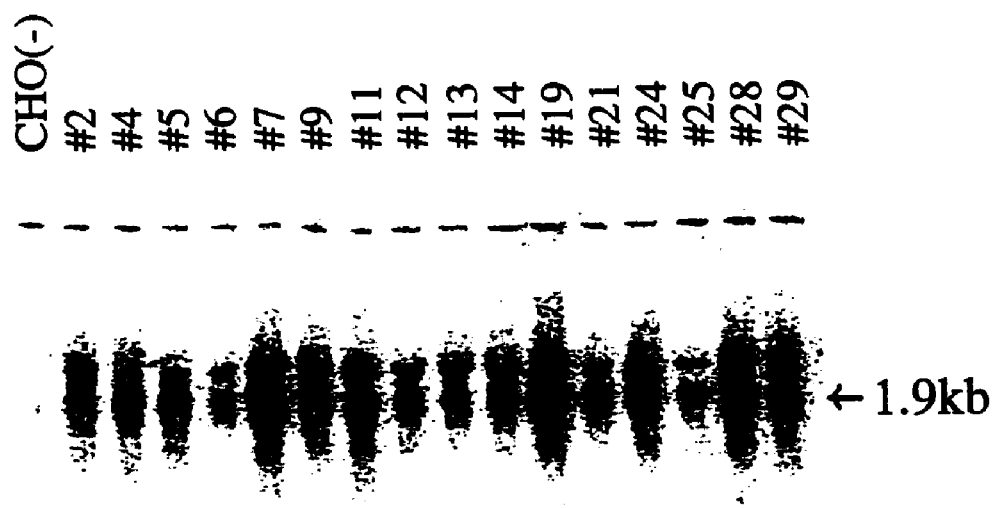
FIG. 1 shows a result of Northern hybridization of the expression of human LPA receptor of the present invention in CHO cells.

The present invention relates to a polypeptide shown in SEQ ID NO:1 in substantially purified form, a homologue thereof, a fragment of the sequence, and a homologue thereof.

Furthermore, the present invention relates to a cDNA encoding these polypeptides. More specifically, it relates to the nucleotide sequence shown in SEQ ID NO:2.

A complementary sequence of the above sequence is also included in the cDNA to be hybridized.

It is preferred that the hybridization conditions are stringent.

The homologue of the polypeptide comprising the amino acid sequence shown in SEQ ID NO:1 is a contiguous amino acid region of usually at least 20 amino acids, preferably at least 30 amino acids, for example 40, 60 or 100 amino acids, which has a homology of at least 70%, preferably at least 80 or 90%, more preferably at least 95%. Such a homologue is hereinafter referred to as the polypeptide of the present invention.

Also, the fragment of the polypeptide comprising the amino acid sequence shown in SEQ ID NO:1 or a fragment of its homologue is a region of at least 10 amino acids, preferably at least 15 amino acid, for example 20, 25, 30, 40, 50 or 60 amino acids.

The cDNA which selectively hybridizes to the CDNA having the nucleotide sequence shown in SEQ ID NO:2 or 3 is a contiguous nucleotide sequence region of usually at least 20 nucleotides, preferably at least 30 nucleotides, for example 40, 60 or 100 nucleotides, which has a homology of at least 70%, preferably at least 80 or 90%, more preferably at least 95%. Such a cDNA is hereinafter referred to as the cDNA of the present invention.

The fragment of the cDNA comprising the nucleotide sequence shown in SEQ ID NO:2 is a contiguous nucleotide sequence region of at least 10 nucleotides, preferably at least 15 nucleotides, for example 20, 25, 30 or 40 nucleotides. Such a fragment is also included in the cDNA of the present invention.

Moreover, the present invention also includes a method for producing the polypeptide of the present invention, comprising culturing the host cell of the present invention under conditions for expressing the polypeptide of the present invention. Preferably, the culturing is carried out under such conditions that the polypeptide of the present invention is expressed and produced by the host cell.

The cDNA of the present invention can produce an antisense mRNA by inserting it into the anfisense region of the above-described vector. Such an antisense mRNA can be used for controlling the level of the polypeptide of the present invention in cells.

The present invention also includes a monoclonal or polyclonal antibody against the polypeptide of the present invention. The present invention also includes a method for producing a monoclonal or polyclonal antibody against the polypeptide of the present invention. The monoclonal antibody can be produced by usual hybridoma techniques using the peptide of the present invention or its fragment as the antigen. The polyclonal antibody can be produced by a general method in which the polypeptide of the present invention is inoculated into a host animal (e.g., rat, rabbit etc.), and the immunized serum is recovered.

The present invention also includes a pharmaceutical composition comprising the polypeptide of the present invention or its antibody and a pharmaceutically acceptable excipient and/or carrier.

In addition to the polypeptide comprising the amino acid sequence shown in SEQ ID NO:1, the polypeptide of the present invention includes those in which a part thereof is deleted (e.g., a polypeptide consisting of only a portion of the SEQ ID NO:1, which is essential for the expression of a biological activity etc.), those in which a portion thereof is substituted with other amino acid (e.g., substituted with an amino acid having a similar physical property), and those in which an amino acid is added to or inserted into a portion thereof.

As is commonly known, 1 to 6 codons encode one amino acid (e.g., one codon for Met, and 6 codons for Leu). Therefore, the nucleotide sequence of the cDNA can be changed without changing the amino acid sequence of the polypeptide.

All of the nucleotide sequences encoding the polypeptide shown in SEQ ID NO:1 are included in the cDNA of the present invention. Productivity of the polypeptide may be improved by changing the nucleotide sequence.

The cDNA shown in the SEQ ID NO:2 is an embodiment of the cDNA of the present invention and represents a native sequence.

The cDNA shown in SEQ ID NO:3 is a sequence in which a native non-translation moiety is added to the cDNA shown in the SEQ ID NO.2.

The CDNA comprising the nucleotide sequence shown in the SEQ ID NO:2 or 3 can be produced, for example, according to the following method. cDNA Cloning of Human LPA Receptor:

Generally, poly(A)$^+$ RNA can be produced by extracting total mRNA from an adult human brain tissue, a human kidney tissue, or the like or from various human cell strains, using a TRIzol reagent (trade name, available from GIBCO BRL) or the like, and by purifying it using a mRNA Purification Kit (trade name, available from Pharmacia) or the like. A cDNA is produced using the method of Gubler et al. (*Gene*, 25:263 (1983)) or a commercially available cDNA synthesis kit, followed by optionally separating a long base pair, and can be introduced into a plasmid vector (e.g., pUC19) or a $\lambda$ phage vector (e.g., $\lambda$gt11).

By carrying out screening of the thus prepared cDNA library by colony hybridization or plaque hybridization using a labeled probe in the usual way, a clone comprising a cDNA fragment containing a region encoding the entire portion of PSP24 human LPA receptor or a part thereof can be selected. Furthermore, optionally, a PSP24 human LPA receptor cDNA can be isolated by again cloning the cDNA into other vector. As a method completely different from this, a partial length of the PSP24 human LPA receptor cDNA can be cloned by PCR by producing primers from the cDNA prepared in the above-described manner, based on the cDNA sequence isolated from Xenopus, and cloning of the complete length can be carried out making use thereof.

BEST MODE FOR CARRYING OUT THE INVENTION

The present invention is illustratively described in the following with reference to examples, but they do not limit the scope of the present invention.

Example 1: Preparation of poly(A)$^+$ RNA and cDNA

Total RNA was extracted from an adult human brain tissue using TRizol reagent (trade name, available from GIBCO BRL), and poly(A)$^+$ RNA was purified using mRNA Purification Kit (trade name, available from Pharmacia).

Based on the poly(A)$^+$ RNA, a cDNA was synthesized using Marathon cDNA Amplification Kit (trade name, available from Clontech).

Example 2: Partial Cloning of PSP24 Human LPA Receptor

Based on the information of nucleotide sequences corresponding to the LPA receptor (PSP24) obtained from Xenopus oocyte, 18 sense primers and the same number of antisense primers were produced, and PCR was carried out among these primers. A band seemed to be a partial fragment of human PSP24 clone was amplified by a combination of certain primers among them. The primer set used in this PCR is shown below.

Xenopus PSP24 Primer #15:
5'-TTCCTTATTATTGTACAGAGGCAGG-3'(25 mer) (SEQ ID NO:4), Xenopus PSP24 Primer #21:
5'-AAGAGMTCAAAATAGTGGTGAAGG-3'(25 mer) (SEQ ID NO:5).

The thus amplified cDNA was fractionated by agarose electrophoresis, linked to pT7Blue-2 T-Vector (trade name, available from Novagen) and then transformed into *Escherichia coli* DH5a to produce a plasmid. Thereafter, the complete nucleotide sequence of this DNA was determined. When the known nucleotide sequences registered in the nucleotide sequence database were searched for the thus determined nucleotide sequence by BLASTN, and the amino acid sequences of known polypeptides registered in the amino acid sequence database were searched for the amino acid sequence translated from the thus determined nucleotide sequence by BLASTP, there was no sequence which showed homology with the Xenopus PSP24 LPA receptor and coincided with the thus determined nucleotide sequence of DNA and amino acid sequence. Accordingly, it was confirmed that this PCR product is a partial length of a novel gene.

Example 3: Complete Length Cloning of PSP24 Human LPA Receptor

Next, complete length cloning was attempted using Marathon cDNA Amplification Kit (trade name, available from Clontech). New primers (F1, F2, F3, R1, R2 and R3) were produced based on the thus determined partial length nucleotide sequence, and 5'-RACE (rapid amplification of cDNA ends) and 3'-RACE were carried out between these primers and 5'-side or 3'-side adapter sequence-specific primers (AP1 and AP2). A band seemed to be a 5'-moiety or 3'-moiety of the PSP24 human LPA receptor clone was amplified by the following combinations of primers among them. The primer sets used in this PCR are shown below.

| 1st PCR | Nested PCR |
|---|---|
| 5'-RACE | |
| R1-AP1 | R2-AP2 |
| R2-AP1 | R3-AP2 |
| R3-AP1 | R3-AP2 |
| 3'-RACE | |
| 1-AP1 | F2-AP2 |
| 2-AP1 | F3-AP2 |

R1 primer:
5'-GCCCATGTCAATGCTCATCTGGAAAGG-3'(27 mer) (SEQ ID NO:6),

R2 primer:
5'-AGGTCTCTGCAGACTCATGAGACCCAG-3'(27 mer) (SEQ ID NO:7),

R3 primer:
5'-GCTGGCCTGGCTGAGGCATATACCTTC-3'(27 mer) (SEQ ID NO:8),

F1 primer:
5'-GTCCAGAGGCAGGATAAGCTAAACCCA-3'(27 mer) (SEQ ID NO:9),

F2 primer:
5'-CCGACCTGCAGATACCTTCCCGAGCTC-3'(27 mer) (SEQ ID NO:10),

F3 primer:
5'-ACCAATCCAGGCTACCAGGCTTATGTG-3'(27 mer) (SEQ ID NO:11)

AP1 primer:
5'-CCATCCTAATACGACTCACTATAGGGC-3'(27 mer) (SEQ ID NO:12):

AP2 primer:
5'-ACTCACTATAGGGCTCGAGCGGC-3'(23 mer) (SEQ ID NO:13).

By subcloning the thus amplified cDNA in the same manner as the partial cloning, the complete nucleotide sequence was determined to obtain the sequence shown in SEQ ID NO:3. Thereafter, the open reading frame was determined and translated into amino acids to obtain the sequence shown in SEQ ID NO:1. When the known nucleotide sequences registered in the nucleotide sequence database were searched by BLASTN, and the amino acid sequences of known polypeptides registered in the amino acid sequence database by BLASTP, there was no sequence which coincided with the nucleotide sequence encoding the polypeptide of the present invention, the PSP24 human LPA receptor. Accordingly, it was confirmed that the polypeptide of the present invention is a novel membrane protein. Also, since there was no homology with similar membrane proteins having seven transmembrane domains, such as PAF receptor, LTB4 receptor and the like, a possibility was suggested that this clone is a human counterpart of the Xenopus PSP24 LPA receptor.

Example 4: Cloning of Complete Length CDNA and Determination of Nucleotide Sequence Cloning of a complete length cDNA was carried out by PCR by producing primers based on the thus determined nucleotide sequence of the PSP24 human LPA receptor shown in SEQ ID NO:3 so as to contain the Kozac sequence and the total translation region. The following two primers were used.

5'-Side Primer:
5'-AAACCATGGTCTTCTCGGCAGTGTTGA-3'(27 mer) (SEQ ID NO:14),

3'-Side Primer:
5'-TCACACCACCGTCCGATGTTCCCCACA-3'(27 mer) (SEQ ID NO:15).

By subcloning the specifically amplified cDNA in the same manner as the partial cloning, the complete nucleotide sequence was determined to obtain the sequence shown in SEQ ID NO:1. Thereafter, the open reading frame was determined and the complete length was isolated.

Example 5: Expression of Protein in Mammal Cells

The receptor of the present invention (PSP24 human LPA receptor) was introduced into CHO cells using a lipofection method to obtain stably character-expressing cells. In order to maximize the receptor expression, the gene was introduced into a vector having a blasticidin-resistant marker, made into a straight chain and then introduced into the cells. Next, the cells were cultured in the presence of blasticidin (5 µg/ml), and 29 resistant strains were isolated by a limiting dilution method. Total RNA was prepared from these clones using TRIzol reagent (Gibco BRL), and expressing clones were selected by RT-PCR. Strength of expression by the expression-confirmed clones was measured by Northern hybridization using the complete length of the gene as a probe (FIG. 1). The numeral shown in the light-side of the drawing indicates the size of a ribosomal RNA used as a size marker, and a band considered to be a transcription product of the gene was observed at around 1.9 kb. As a control, electrophoresis of the total RNA prepared from CHO cells of the parent strain was carried out and shown in the left-side end.

What is claimed is:

1. A protein comprising the amino acid sequence shown in SEQ ID No:1.

2. A human lysophosphatidic acid (human LPA) receptor comprising the amino acid sequence shown in SEQ ID NO:1.

3. A method for screening a human LPA-like substance, a human LPA antagonist, and an antagonist or agonist for a phospholipid other than LPA capable of responding to the human LPA receptor, comprising using the protein according to claim 1 or 2.

4. A human LPA inhibitor or an inhibitor for a phospholipid other than human LPA, comprising the protein according to claim 1 or 2 as an active ingredient.

5. A method for producing a human LPA receptor, comprising culturing a cell transformed with an expression vector carrying a DNA fragment encoding the protein according to claim 1 or 2, and recovering the protein from the cultured mixture.

6. A monoclonal or polyclonal antibody which specifically binds to the protein according to claims 1 and 2.

7. A cDNA encoding the polypeptide comprising the amino sequence shown in SEQ ID NO:1.

8. A CDNA according to claim 7 comprising the nucleotide sequence shown in SEQ ID NO:2.

9. A cDNA according to claim 7 comprising the nucleotide sequence shown in SEQ ID NO:3.

10. A replication or expression vector carrying the cDNA according to any one of claims 7 to 9.

11. A host cell transformed with the replication or expression vector according to claim 10.

* * * * *

SEQUENCE LISTING

<160> NUMBER OF SEQ ID NOS: 15

<210> SEQ ID NO: 1
<211> LENGTH: 419
<212> TYPE: PRT
<213> ORGANISM: Homo sapiens

<400> SEQUENCE: 1

Met Val Phe Ser Ala Val Leu Thr Ala Phe His Thr Gly Thr Ser Asn
 1               5                  10                  15

Thr Thr Phe Val Val Tyr Glu Asn Thr Tyr Met Asn Ile Thr Leu Pro
             20                  25                  30

Pro Pro Phe Gln His Pro Asp Leu Ser Pro Leu Leu Arg Tyr Ser Phe
         35                  40                  45

Glu Thr Met Ala Pro Thr Gly Leu Ser Ser Leu Thr Val Asn Ser Thr
     50                  55                  60

Ala Val Pro Thr Thr Pro Ala Ala Phe Lys Ser Leu Asn Leu Pro Leu
 65                  70                  75                  80

Gln Ile Thr Leu Ser Ala Ile Met Ile Phe Ile Leu Phe Val Ser Phe
                 85                  90                  95

Leu Gly Asn Leu Val Val Cys Leu Met Val Tyr Gln Lys Ala Ala Met
             100                 105                 110

Arg Ser Ala Ile Asn Ile Leu Leu Ala Ser Leu Ala Phe Ala Asp Met
         115                 120                 125

Leu Leu Ala Val Leu Asn Met Pro Phe Ala Leu Val Thr Ile Leu Thr
     130                 135                 140

Thr Arg Trp Ile Phe Gly Lys Phe Phe Cys Arg Val Ser Ala Met Phe
145                 150                 155                 160

Phe Trp Leu Phe Val Ile Glu Gly Val Ala Ile Leu Leu Ile Ile Ser
                 165                 170                 175

Ile Asp Arg Phe Leu Ile Ile Val Gln Arg Gln Asp Lys Leu Asn Pro
             180                 185                 190

Tyr Arg Ala Lys Val Leu Ile Ala Val Ser Trp Ala Thr Ser Phe Cys
         195                 200                 205

Val Ala Phe Pro Leu Ala Val Gly Asn Pro Asp Leu Gln Ile Pro Ser
     210                 215                 220

Arg Ala Pro Gln Cys Val Phe Gly Tyr Thr Thr Asn Pro Gly Tyr Gln
225                 230                 235                 240

Ala Tyr Val Ile Leu Ile Ser Leu Ile Ser Phe Phe Ile Pro Phe Leu
                 245                 250                 255

Val Ile Leu Tyr Ser Phe Met Gly Ile Leu Asn Thr Leu Arg His Asn
             260                 265                 270

Ala Leu Arg Ile His Ser Tyr Pro Glu Gly Ile Cys Leu Ser Gln Ala
         275                 280                 285

Ser Lys Leu Gly Leu Met Ser Leu Gln Arg Pro Phe Gln Met Ser Ile
     290                 295                 300

Asp Met Gly Phe Lys Thr Arg Ala Phe Thr Thr Ile Leu Ile Leu Phe
305                 310                 315                 320

Ala Val Phe Ile Val Cys Trp Ala Pro Phe Thr Thr Tyr Ser Leu Val
                 325                 330                 335

Ala Thr Phe Ser Lys His Phe Tyr Gln His Asn Phe Phe Glu Ile
         340                 345                 350

Ser Thr Trp Leu Leu Trp Leu Cys Tyr Leu Lys Ser Ala Leu Asn Pro

|  | 355 |  |  |  | 360 |  |  |  | 365 |  |  |
|---|---|---|---|---|---|---|---|---|---|---|---|
| Leu | Ile | Tyr | Tyr | Trp | Arg | Ile | Lys | Lys | Phe | His | Asp | Ala | Cys | Leu | Asp |
|  |  | 370 |  |  |  |  | 375 |  |  |  |  | 380 |  |  |  |
| Met | Met | Pro | Lys | Ser | Phe | Lys | Phe | Leu | Pro | Gln | Leu | Pro | Gly | His | Thr |
| 385 |  |  |  |  | 390 |  |  |  |  | 395 |  |  |  |  | 400 |
| Lys | Arg | Arg | Ile | Arg | Pro | Ser | Ala | Val | Tyr | Val | Cys | Gly | Glu | His | Arg |
|  |  |  |  | 405 |  |  |  |  | 410 |  |  |  |  | 415 |  |
| Thr | Val | Val |

<210> SEQ ID NO: 2
<211> LENGTH: 1257
<212> TYPE: DNA
<213> ORGANISM: Homo sapiens

<400> SEQUENCE: 2

| atggtcttct | cggcagtgtt | gactgcgttc | cataccggga | catccaacac | aacatttgtc | 60 |
| gtgtatgaaa | acacctacat | gaatattaca | ctccctccac | cattccagca | tcctgacctc | 120 |
| agtccattgc | ttagatatag | ttttgaaacc | atggctccca | ctggtttgag | ttccttgacc | 180 |
| gtgaatagta | cagctgtgcc | cacaacacca | gcagcattta | agagcctaaa | cttgcctctt | 240 |
| cagatcaccc | tttctgctat | aatgatattc | attctgtttg | tgtcttttct | tgggaacttg | 300 |
| gttgtttgcc | tcatggttta | ccaaaaagct | gccatgaggt | ctgcaattaa | catcctcctt | 360 |
| gccagcctag | cttttgcaga | catgttgctt | gcagtgctga | acatgccctt | tgccctggta | 420 |
| actattctta | ctacccgatg | gatttttggg | aaattcttct | gtagggtatc | tgctatgttt | 480 |
| ttctggttat | ttgtgataga | aggagtagcc | atcctgctca | tcattagcat | agataggttc | 540 |
| cttattatag | tccagaggca | ggataagcta | aacccatata | gagctaaggt | tctgattgca | 600 |
| gtttcttggg | caacttcctt | ttgtgtagct | tttccttag | ccgtaggaaa | ccccgacctg | 660 |
| cagataccct | cccgagctcc | ccagtgtgtg | tttgggtaca | caaccaatcc | aggctaccag | 720 |
| gcttatgtga | ttttgatttc | tctcatttct | ttcttcatac | ccttcctggt | aatactgtac | 780 |
| tcatttatgg | gcatactcaa | cacccttcgg | cacaatgcct | tgaggatcca | tagctaccct | 840 |
| gaaggtatat | gcctcagcca | ggccagcaaa | ctgggtctca | tgagtctgca | gagacctttc | 900 |
| cagatgagca | ttgacatggg | ctttaaaaca | cgtgccttca | ccactatttt | gattctcttt | 960 |
| gctgtcttca | ttgtctgctg | ggccccattc | accacttaca | gccttgtggc | aacattcagt | 1020 |
| aagcactttt | actatcagca | caacttttt | gagattagca | cctggctact | gtggctctgc | 1080 |
| tacctcaagt | ctgcattgaa | tccgctgatc | tactactgga | ggattaagaa | attccatgat | 1140 |
| gcttgcctgg | acatgatgcc | taagtccttc | aagttttgc | cgcagctccc | tggtcacaca | 1200 |
| aagcgacgga | tacgtcctag | tgctgtctat | gtgtgtgggg | aacatcggac | ggtggtg | 1257 |

<210> SEQ ID NO: 3
<211> LENGTH: 1892
<212> TYPE: DNA
<213> ORGANISM: Homo sapiens
<220> FEATURE:
<221> NAME/KEY: CDS
<222> LOCATION: (208)..(1464)

<400> SEQUENCE: 3

| tggagccatg | ctccctgggc | tcttccgcgg | gcgcccgcgc | gctgcccttc | gcttgaggca | 60 |
| aaaggactct | tgtggaagat | ggaactcatt | gtccattttc | cagaatgtat | ttccaagccc | 120 |
| atcaatggga | cctgatactg | ctgttctgtg | ttgaaatgct | tgaagaactc | ctgcatctct | 180 |

-continued

```
gcttgcatct tccatcctac tgaaacc atg gtc ttc tcg gca gtg ttg act gcg        234
                             Met Val Phe Ser Ala Val Leu Thr Ala
                              1               5 ttc cat acc ggg aca tcc aac aca aca ttt gtc gtg tat gaa aac acc          282
Phe His Thr Gly Thr Ser Asn Thr Thr Phe Val Val Tyr Glu Asn Thr
 10              15                  20                  25 tac atg aat att aca ctc cct cca cca ttc cag cat cct gac ctc agt          330
Tyr Met Asn Ile Thr Leu Pro Pro Pro Phe Gln His Pro Asp Leu Ser
                 30                  35                  40 cca ttg ctt aga tat agt ttt gaa acc atg gct ccc act ggt ttg agt          378
Pro Leu Leu Arg Tyr Ser Phe Glu Thr Met Ala Pro Thr Gly Leu Ser
             45                  50                  55 tcc ttg acc gtg aat agt aca gct gtg ccc aca aca cca gca gca ttt          426
Ser Leu Thr Val Asn Ser Thr Ala Val Pro Thr Thr Pro Ala Ala Phe
         60                  65                  70 aag agc cta aac ttg cct ctt cag atc acc ctt tct gct ata atg ata          474
Lys Ser Leu Asn Leu Pro Leu Gln Ile Thr Leu Ser Ala Ile Met Ile
     75                  80                  85 ttc att ctg ttt gtg tct ttt ctt ggg aac ttg gtt gtt tgc ctc atg          522
Phe Ile Leu Phe Val Ser Phe Leu Gly Asn Leu Val Val Cys Leu Met
 90                  95                 100                 105 gtt tac caa aaa gct gcc atg agg tct gca att aac atc ctc ctt gcc          570
Val Tyr Gln Lys Ala Ala Met Arg Ser Ala Ile Asn Ile Leu Leu Ala
                110                 115                 120 agc cta gct ttt gca gac atg ttg ctt gca gtg ctg aac atg ccc ttt          618
Ser Leu Ala Phe Ala Asp Met Leu Leu Ala Val Leu Asn Met Pro Phe
            125                 130                 135 gcc ctg gta act att ctt act acc cga tgg att ttt ggg aaa ttc ttc          666
Ala Leu Val Thr Ile Leu Thr Thr Arg Trp Ile Phe Gly Lys Phe Phe
        140                 145                 150 tgt agg gta tct gct atg ttt ttc tgg tta ttt gtg ata gaa gga gta          714
Cys Arg Val Ser Ala Met Phe Phe Trp Leu Phe Val Ile Glu Gly Val
    155                 160                 165 gcc atc ctg ctc atc att agc ata gat agg ttc ctt att ata gtc cag          762
Ala Ile Leu Leu Ile Ile Ser Ile Asp Arg Phe Leu Ile Ile Val Gln
170                 175                 180                 185 agg cag gat aag cta aac cca tat aga gct aag gtt ctg att gca gtt          810
Arg Gln Asp Lys Leu Asn Pro Tyr Arg Ala Lys Val Leu Ile Ala Val
                190                 195                 200 tct tgg gca act tcc ttt tgt gta gct ttt cct tta gcc gta gga aac          858
Ser Trp Ala Thr Ser Phe Cys Val Ala Phe Pro Leu Ala Val Gly Asn
            205                 210                 215 ccc gac ctg cag ata cct tcc cga gct ccc cag tgt gtg ttt ggg tac          906
Pro Asp Leu Gln Ile Pro Ser Arg Ala Pro Gln Cys Val Phe Gly Tyr
        220                 225                 230 aca acc aat cca ggc tac cag gct tat gtg att tgg att tct ctc att          954
Thr Thr Asn Pro Gly Tyr Gln Ala Tyr Val Ile Leu Ile Ser Leu Ile
    235                 240                 245 tct ttc ttc ata ccc ttc ctg gta ata ctg tac tca ttt atg ggc ata         1002
Ser Phe Phe Ile Pro Phe Leu Val Ile Leu Tyr Ser Phe Met Gly Ile
250                 255                 260                 265 ctc aac acc ctt cgg cac aat gcc ttg agg atc cat agc tac cct gaa         1050
Leu Asn Thr Leu Arg His Asn Ala Leu Arg Ile His Ser Tyr Pro Glu
                270                 275                 280 ggt ata tgc ctc agc cag gcc agc aaa ctg ggt ctc atg agt ctg cag         1098
Gly Ile Cys Leu Ser Gln Ala Ser Lys Leu Gly Leu Met Ser Leu Gln
            285                 290                 295 aga cct ttc cag atg agc att gac atg ggc ttt aaa aca cgt gcc ttc         1146
Arg Pro Phe Gln Met Ser Ile Asp Met Gly Phe Lys Thr Arg Ala Phe
```

-continued

```
              300                 305                 310
acc act att ttg att ctc ttt gct gtc ttc att gtc tgc tgg gcc cca       1194
Thr Thr Ile Leu Ile Leu Phe Ala Val Phe Ile Val Cys Trp Ala Pro
    315                 320                 325 ttc acc act tac agc ctt gtg gca aca ttc agt aag cac ttt tac tat       1242
Phe Thr Thr Tyr Ser Leu Val Ala Thr Phe Ser Lys His Phe Tyr Tyr
330                 335                 340                 345 cag cac aac ttt ttt gag att agc acc tgg cta ctg tgg ctc tgc tac       1290
Gln His Asn Phe Phe Glu Ile Ser Thr Trp Leu Leu Trp Leu Cys Tyr
                350                 355                 360 ctc aag tct gca ttg aat ccg ctg atc tac tac tgg agg att aag aaa       1338
Leu Lys Ser Ala Leu Asn Pro Leu Ile Tyr Tyr Trp Arg Ile Lys Lys
            365                 370                 375 ttc cat gat gct tgc ctg gac atg atg cct aag tcc ttc aag ttt ttg       1386
Phe His Asp Ala Cys Leu Asp Met Met Pro Lys Ser Phe Lys Phe Leu
        380                 385                 390 ccg cag ctc cct ggt cac aca aag cga cgg ata cgt cct agt gct gtc       1434
Pro Gln Leu Pro Gly His Thr Lys Arg Arg Ile Arg Pro Ser Ala Val
    395                 400                 405 tat gtg tgt ggg gaa cat cgg acg gtg gtg tgaatattgg aactggctga        1484
Tyr Val Cys Gly Glu His Arg Thr Val Val
410                 415 cattttgggt gatgcttgtt ctttattgac attgaattct ctttctcata gcctctccac    1544
tttatttttt tttataggt ttgtgtatgt atgtgtgtga gcagtgtaaa gaaagaatgg     1604
taattatagt tctgttacca agaataaata ataggaaagt gattacaaat attacctcca   1664
gggttcaata gaaatcctca atttaggtgt aggagacttt tttttggttt tggggttttt   1724
ccttgattga ttttgttttc atagtgggaa tcaggattgt gctttattga gcctgcagtt   1784
acattgaatt gtaggtgttt cgtgtgctgc taaggtatgc ttatttgagt ttatcaagac   1844
tttttttttt ctggaagaca ctgctgcttt taccatcaca ttggagcc               1892
```

<210> SEQ ID NO: 4
<211> LENGTH: 25
<212> TYPE: DNA
<213> ORGANISM: Xenopus laeuis
<220> FEATURE:
<223> OTHER INFORMATION: PSP24 primer #15

<400> SEQUENCE: 4
ttccttatta ttgtacagag gcagg                                          25

<210> SEQ ID NO: 5
<211> LENGTH: 25
<212> TYPE: DNA
<213> ORGANISM: Xenopus laeuis
<220> FEATURE:
<223> OTHER INFORMATION: PSP24 primer #21

<400> SEQUENCE: 5
aagagaatca aaatagtggt gaagg                                          25

<210> SEQ ID NO: 6
<211> LENGTH: 27
<212> TYPE: DNA
<213> ORGANISM: Artificial Sequence
<220> FEATURE:
<223> OTHER INFORMATION: Description of Artificial Sequence: R1 primer

<400> SEQUENCE: 6
gcccatgtca atgctcatct ggaaagg                                        27

<210> SEQ ID NO: 7
<211> LENGTH: 27
<212> TYPE: DNA
<213> ORGANISM: Artificial Sequence
<220> FEATURE:
<223> OTHER INFORMATION: Description of Artificial Sequence: R2 primer

<400> SEQUENCE: 7
aggtctctgc agactcatga gacccag 27

<210> SEQ ID NO: 8
<211> LENGTH: 27
<212> TYPE: DNA
<213> ORGANISM: Artificial Sequence
<220> FEATURE:
<223> OTHER INFORMATION: Description of Artificial Sequence: R3 primer

<400> SEQUENCE: 8
gctggcctgg ctgaggcata taccttc 27

<210> SEQ ID NO: 9
<211> LENGTH: 27
<212> TYPE: DNA
<213> ORGANISM: Artificial Sequence
<220> FEATURE:
<223> OTHER INFORMATION: Description of Artificial Sequence: F1 primer

<400> SEQUENCE: 9
gtccagaggc aggataagct aaaccca 27

<210> SEQ ID NO: 10
<211> LENGTH: 27
<212> TYPE: DNA
<213> ORGANISM: Artificial Sequence
<220> FEATURE:
<223> OTHER INFORMATION: Description of Artificial Sequence: F2 primer

<400> SEQUENCE: 10
ccgacctgca gataccttcc cgagctc 27

<210> SEQ ID NO: 11
<211> LENGTH: 27
<212> TYPE: DNA
<213> ORGANISM: Artificial Sequence
<220> FEATURE:
<223> OTHER INFORMATION: Description of Artificial Sequence: F3 primer

<400> SEQUENCE: 11
accaatccag gctaccaggc ttatgtg 27

<210> SEQ ID NO: 12
<211> LENGTH: 27
<212> TYPE: DNA
<213> ORGANISM: Unknown
<220> FEATURE:
<223> OTHER INFORMATION: Description of Unknown Sequence: 5'Race adaptor
      primer: AP1 primer

<400> SEQUENCE: 12
ccatcctaat acgactcact atagggc 27

<210> SEQ ID NO: 13
<211> LENGTH: 23
<212> TYPE: DNA
<213> ORGANISM: Unknown

```
<220> FEATURE:
<223> OTHER INFORMATION: Description of Unknown Sequence: 3'Race adaptor
      primer: AP1 primer

<400> SEQUENCE: 13
actcactata gggctcgagc ggc                                              23

<210> SEQ ID NO: 14
<211> LENGTH: 27
<212> TYPE: DNA
<213> ORGANISM: Artificial Sequence
<220> FEATURE:
<223> OTHER INFORMATION: Description of Artificial Sequence: 5'end
      primer coding kozac sequence and all transcription region of PSP24
      type human lysophosphatidic acid receptor

<400> SEQUENCE: 14
aaaccatggt cttctcggca gtgttga                                          27

<210> SEQ ID NO: 15
<211> LENGTH: 27
<212> TYPE: DNA
<213> ORGANISM: Artificial Sequence
<220> FEATURE:
<223> OTHER INFORMATION: Description of Artificial Sequence: 3'end
      primer coding kozac sequence and all transcription region of PSP24
      type human lysophosphatidic acid receptor

<400> SEQUENCE: 15
tcacaccacc gtccgatgtt ccccaca                                          27
```